US010107780B2

(12) United States Patent
Strong

(10) Patent No.: US 10,107,780 B2
(45) Date of Patent: Oct. 23, 2018

(54) DIP-STICK WESTERN BLOT

(71) Applicant: Bio-Rad Laboratories, Inc., Hercules, CA (US)

(72) Inventor: William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 179 days.

(21) Appl. No.: 14/644,527

(22) Filed: Mar. 11, 2015

(65) Prior Publication Data

US 2015/0260681 A1 Sep. 17, 2015

Related U.S. Application Data

(60) Provisional application No. 61/951,148, filed on Mar. 11, 2014.

(51) Int. Cl.
*G01N 27/447* (2006.01)
*G01N 33/543* (2006.01)
*G01N 30/90* (2006.01)

(52) U.S. Cl.
CPC . *G01N 27/44739* (2013.01); *G01N 33/54386* (2013.01); *G01N 30/90* (2013.01)

(58) Field of Classification Search
CPC ....... G01N 27/44739; G01N 33/54386; G01N 30/90
See application file for complete search history.

(56) References Cited

U.S. PATENT DOCUMENTS 5,126,025 A 6/1992 Carson et al.
5,476,016 A * 12/1995 Fedorka-Cray .............
G01N 27/44704
378/162

(Continued)

FOREIGN PATENT DOCUMENTS

EP 1325151 B1 7/2003
WO 88/08534 A1 11/1988

(Continued)

OTHER PUBLICATIONS

Georges et al. Enhancing the sensitivity of DNA detection and recovery from agarose gels, 1998, Electrophoresis, vol. 9, pp. 213-216.*

(Continued)

*Primary Examiner* — Melanie Yu Brown
(74) *Attorney, Agent, or Firm* — Kilpatrick Townsend and Stockton LLP

(57) ABSTRACT

Methods, kits, and systems are provided for separating, immobilizing, and/or detecting analytes of one or more samples using dipsticks. A 'dipstick' is an object that can be embedded and subsequently removed from a separation medium, and to which analytes can be immobilized while the object is embedded in the separation medium. Examples of separation media include an electrophoresis gel of any format and a stationary phase for column chromatography. Embodiments of the present methods include applying a sample to a separation medium; separating analytes of the sample in the separation medium along a separation axis; immobilizing the analytes on a dipstick embedded in the separation medium; removing the dipstick from the separation medium; and detecting the analytes immobilized on the removed dipstick.

16 Claims, 4 Drawing Sheets

(56) References Cited

U.S. PATENT DOCUMENTS

| | | | |
|---|---|---|---|
| 5,593,561 A * | 1/1997 | Cognard | B01D 57/02 204/456 |
| 6,129,828 A * | 10/2000 | Sheldon, III | B01D 57/02 204/465 |
| 6,316,607 B1 * | 11/2001 | Massey | C07D 473/08 435/6.11 |
| 6,716,641 B1 | 4/2004 | Sundrehagan | |
| 7,846,676 B2 | 12/2010 | Yang et al. | |
| 7,935,308 B2 | 5/2011 | O'Neill et al. | |
| 7,935,489 B2 | 5/2011 | O'Neill et al. | |
| 8,021,611 B2 | 9/2011 | Roach et al. | |
| 2004/0053321 A1 | 3/2004 | Koren et al. | |
| 2005/0161326 A1 * | 7/2005 | Morita | B01F 5/061 204/450 |
| 2007/0015230 A1 | 1/2007 | Hammond et al. | |
| 2008/0017512 A1 | 1/2008 | Bordunov et al. | |
| 2008/0118983 A1 * | 5/2008 | Wang | G01N 27/44739 436/63 |
| 2011/0300531 A1 | 12/2011 | Bohannon | |
| 2012/0142904 A1 * | 6/2012 | He | B01D 57/02 530/412 |
| 2012/0213667 A1 | 8/2012 | Roach et al. | |
| 2012/0220049 A1 | 8/2012 | Bunce et al. | |
| 2012/0329040 A1 | 12/2012 | Herr et al. | |
| 2013/0115714 A1 | 5/2013 | Macnamara et al. | |
| 2013/0213811 A1 | 8/2013 | Kennedy et al. | |

FOREIGN PATENT DOCUMENTS

| | | |
|---|---|---|
| WO | 2011/144758 A1 | 11/2011 |
| WO | 2013/180642 A1 | 12/2013 |

OTHER PUBLICATIONS

International Search Report and Written Opinion from PCT/US2014/059710, dated Jan. 9, 2015.

Anderson et al.; "Western Blotting Using Capillary Electrophoresis," *Anal. Chem.* (2011) 83(4):1350-5. doi: 10.1021/ac102671n. Epub Jan. 25, 2011.

Jin et al., "Western Blotting using Microchip Electrophoresis Interfaced to a Protein Capture Membrane," *Anal. Chem.* (2013) 85(12):6073-6079. doi: 10.1021/ac400940x. Epub May 28, 2013.

U.S. Appl. No. 14/558,541, filed Dec. 2, 2014 by William Strong.

Kim et al. "Microfluidic Western Blotting: Cationic surfactant based protein sizing integrated with electrostatic immobilization", IEEE, US, pp. 197-200, Jan. 23, 2011.

Extended European Search Report from EP Appln. No. 15761295.3, dated Jan. 17, 2017.

Barelli, S. et al.; "Oxidation of proteins: Basic principles and perspectives for blood proteomics"; *Proteomics Clin. Appl.*; vol. 2; 2008; pp. 142-157.

Floegel, U. et al.; "Determination of De Novo Synthesized Amino Acids in Cellular Proteins Revisited by $^{13}C$ NMR Spectroscopy"; *NMR in Biomedicine;* vol. 10; 1997; pp. 50-58.

Menter, P; "Acrylamide Polymerization—A Practical Approach"; Electrophoresis Tech Note 1156; Apr. 2001; 8 pages.

Toennies, G.; "The Oxidative Conversion of Casein Into Protein Free of Methionine and Tryptophane"; *J. Biol. Chem.;* vol. 145; 1942; pp. 667-670.

\* cited by examiner

DIP-STICK WESTERN BLOT

CROSS-REFERENCES TO RELATED APPLICATIONS

The present application claims priority to U.S. Provisional Application No. 61/951,148, entitled "DIP-STICK WESTERN BLOT" and filed Mar. 11, 2014, the entire contents of which are incorporated herein by reference for all purposes.

BACKGROUND OF THE INVENTION

Electroblotting is a widely used technique in biotechnology. The technique involves applying a potential difference across a matrix in which charged analytes, such as DNA, RNA, or protein, are distributed. The potential difference causes the analytes to migrate out of the matrix and become deposited on a surface or 'blot' next to the matrix, where they are immobilized. The analytes can then be detected using fluorescence, chemiluminescence, radioactivity, or other phenomena, by probing the analytes with one or more detectable binding partners.

Electroblotting is often paired with, and performed immediately after, a technique such as electrophoresis that separates the analytes in the matrix on the basis of size or charge. Thus, electroblotting provides a way to interrogate a biological sample on the basis of characteristics orthogonal or complementary to those accessible by electrophoresis. For example, a protein sample can be subjected to electrophoresis in a polyacrylamide gel and then transferred to a nitrocellulose membrane by electroblotting. The migration rates of proteins in the gel can reflect their molecular weights, and the affinities of these proteins for binding partners on the membrane can reflect whether the proteins contain certain sequence motifs. Because electroblotting follows electrophoresis and can preserve the separation of analytes achieved by electrophoresis, detection of analytes on a blot can reveal multiple levels of information about the sample from which the analytes originate.

Various kinds of electroblotting are known and practiced in the art. When the analytes are DNA fragments, the transfer of the analytes out of a gel or other matrix and onto a blot is called Southern blotting after its originator, the British biologist Edwin M. Southern. By analogy, the transfer of RNA fragments is termed northern blotting, and the transfer of proteins or polypeptides is termed western blotting. Still further examples are "eastern" blots for post-translational modifications, and "far western" blots for protein interactions. Some of these blotting techniques can be performed in the absence of an applied potential difference, with the transfer of analytes from the matrix to the blot instead driven by capillary action.

To carry out electroblotting as it is typically practiced, a complex procedure is required. After separating analytes in the matrix, such as by electrophoresis, the matrix and blot must be precisely juxtaposed to facilitate the transfer of analytes. Next, electrodes and other apparatus must be assembled around the matrix and blot. The apparatus can include a buffer reservoir, sponges, or wetted paper to allow current to flow between the electrodes. A potential difference is then applied between the electrodes and transfer occurs. Before analytes can be detected, however, the apparatus must be disassembled and the blot must be removed from the matrix and handled further. The handling is required to expose analytes of interest on the blot to binding partners in a controlled manner. For example, in the case of western blotting, the blot may be incubated with a blocking protein that binds the blot non-specifically, a primary antibody that binds specifically to an analyte of interest, and a labeled secondary antibody that binds to the primary antibody. Each of these incubations requires submerging the blot in a different solution. Detection then can involve placing the blot next to a piece of film or an optical scanner sensitive to a label on one of the binding partners.

The electroblotting procedure is costly on several levels. The procedure is time consuming, in some cases taking place over the course of several days, and is not easily automated. The blot must be mechanically manipulated in several different ways, and these manipulations require care to ensure, for example, that the matrix and blot do not break, or that the blot does not come into contact with contaminants. Thus, the procedure requires a highly skilled, extensively trained practitioner to execute successfully. Electroblotting is also costly in terms of reagents. The blot is often incubated with a large excess of binding partners in order to detect analytes with adequate sensitivity, even though these analytes may occupy only a small portion of the surface area of the blot.

Electroblotting also does not always yield reproducible or quantitative data. Variability in sample size, transfer efficiency, and the affinities of binding partners for analytes can result in insensitive or imprecise detection. The same analyte may not be detectable at the same level from one electroblotting procedure to the next, and differences in the signals arising from the analyte in separate procedures may not reflect differences in the abundance or integrity of the analyte. Similarly, the signals arising from two different analytes in the same procedure may not accurately reflect the relative concentrations of these analytes. In addition, many electroblotting procedures allow detection of only a subset of the analytes present in the sample, and preclude detection of analytes on the matrix. Thus, information about the composition of the sample (for example, the distribution of protein molecular weights) can be lost upon transferring analytes from the matrix to the blot.

SUMMARY OF THE INVENTION

Provided herein are methods, kits, and systems for separating, immobilizing, and/or detecting analytes of one or more samples using dipsticks. Also provided are dipsticks for use in some embodiments of the invention.

A method of separating and detecting analytes of a sample is provided. The method includes: applying a sample to a separation medium; separating analytes of the sample in the separation medium along a separation axis; immobilizing the analytes on a dipstick embedded in the separation medium; removing the dipstick from the separation medium; and detecting the analytes immobilized on the removed dipstick.

In some embodiments of the method, separating analytes of the sample includes performing electrophoresis, electroosmosis, or isoelectric focusing. The separation medium can include a gel in a slab, tube, cassette, slide, capillary, comb, mini-card, open mold, or microfluidic chip-like format. Alternatively or in addition, the separation medium can include a polymer matrix, hydrogel, or crosslinked polymer, such as dextran, agarose, polyacrylamide, polyacrylamide-bis-acrylamide, or N,N-polydimethylacrylamide. The separation medium can also include a denaturant. In some embodiments, the separation medium includes a chromatography resin, and separating analytes of the sample includes flowing the sample through the chromatography resin. In some embodiments, the separation medium includes a fluid channel and separating analytes of the sample comprises flowing the sample through the fluid channel.

In some aspects of the method, immobilizing the analytes on the dipstick includes covalently linking the analytes to the dipstick. This can involve crosslinking the analytes to the dipstick. In other aspects, immobilizing the analytes on the dipstick includes non-covalently linking the analytes to the dipstick. This can involve binding the analytes to an affinity structure. The affinity structure can include an antibody, enzyme, protein, peptide, aptamer, ligand, nucleic acid, nucleotide, nucleic acid analog, coordination complex, natural or synthetic polymer, carbohydrate, or small molecule. In some cases, the analytes are proteins and the affinity structure includes an antibody. Alternatively or in addition, immobilizing the analytes on the dipstick can include depositing the analytes on a membrane coupled to the dipstick. The membrane can include nitrocellulose or polyvinylidene fluoride.

In some embodiments of the method, the analytes are immobilized on the dipstick by adsorption, electrostatic interactions, ionic interactions, or hydrophobic interactions. In some embodiments, immobilizing the analytes on the dipstick includes exposing the dipstick to light, heat, or an altered chemical environment. In some embodiments, immobilizing the analytes on the dipstick comprises exposing the dipstick to fixation reagents. The analytes can be immobilized on the dipstick non-specifically. The dipstick includes an electrode in some embodiments, and immobilizing the analytes on the dipstick can involve energizing the electrode. The dipstick can also include a magnet, and immobilizing the analytes on the dipstick can include drawing magnetic labels linked to the analytes toward the magnet.

In the present method, detecting the analytes immobilized on the removed dipstick includes, in some embodiments, optically detecting the analytes or labels linked to the analytes. In some embodiments, detection includes contacting the removed dipstick with a binding partner for one or more analytes of the sample, and detecting a signal indicative of binding between the binding partner and the one or more analytes. The binding partner can include an antibody, enzyme, protein, peptide, aptamer, ligand, nucleic acid, nucleotide, nucleic acid analog, coordination complex, natural or synthetic polymer, carbohydrate, or small molecule. In some cases, the analytes are proteins and the binding partner includes an antibody. The signal can include chemiluminescence, electroluminescence, fluorescence, infrared radiation, radioactivity, color, or optical absorbance, and can arise from surface plasmon resonance. In some embodiments, detecting a signal includes exposing the binding partner to a reagent that binds to or reacts with the binding partner. In some embodiments of the method, detecting the analytes on the removed dipstick includes, alternatively or in addition, applying a blocking agent to the dipstick.

The method can include additional steps. In some embodiments, the method also includes embedding the dipstick in the separation medium. This can occur before separating the analytes or after separating the analytes. Embedding the dipstick in the separation medium can include piercing, cutting or slicing the separation medium. In some embodiments, the method also includes depositing control analytes on the dipstick prior to embedding the dipstick in the separation medium.

In some embodiments, the separation medium is retained in a supporting structure, and the method also includes moving the dipstick within the supporting structure prior to immobilizing the analytes on the dipstick. The dipstick can be moved in a direction perpendicular to the separation axis. Alternatively or in addition, the method can include applying control analytes to the separation medium and separating the control analytes in the separation medium along the separation axis. In some embodiments, the method also includes denaturing the analytes, or eluting one or more analytes from the removed dipstick.

Dipsticks can have various characteristics in embodiments of the method. The dipstick can be elongated and aligned parallel or perpendicular to the separation axis. The dipstick can be porous. The dipstick can include a texture or beaded coating that increases the surface area of the dipstick. Alternatively or in addition, the dipstick can be decorated with beads. The dipstick can include glass, plastic, ceramic, metal, carbon fiber, graphite, or a copolymer, and can be shaped into a rod, blade, sheet, wire, needle, or thread. In some embodiments of the method, the dipstick is electrically or thermally conductive. In other embodiments, the dipstick is electrically or thermally insulating.

In some embodiments, the dipstick includes a capture agent. The capture agent can be a crosslinker or an affinity structure, for example. The affinity structure can include an antibody, enzyme, protein, peptide, aptamer, ligand, nucleic acid, nucleotide, nucleic acid analog, coordination complex, natural or synthetic polymer, carbohydrate, or small molecule. Alternatively or in addition, the capture agent can be a membrane. In some embodiments, the membrane includes nitrocellulose or polyvinylidene fluoride.

The dipstick can also include a handle portion in some embodiments. The handle portion can include printed markings to facilitate identification of the sample or analytes immobilized on the dipstick. In some embodiments of the method, the separation medium is enclosed in a supporting structure and the supporting structure includes the dipstick.

Another method is also provided herein for separating and detecting analytes of a plurality of samples. The method includes: applying a plurality of samples to a separation medium; separating analytes of the samples in the separation medium along a separation axis; immobilizing the analytes on a plurality of dipsticks embedded in the separation medium, wherein at least one dipstick is associated with each sample; removing the dipsticks from the separation medium; and detecting the analytes on the removed dipsticks.

In some embodiments of this method, two dipsticks of the plurality of dipsticks are configured for immobilizing different analytes. The two dipsticks can be associated with the same sample. In some embodiments, the separation medium is a slab gel and each dipstick is aligned to one lane of the slab gel.

In still another method provided herein, analytes of a plurality of samples can be separated and detected. The method includes: applying a plurality of samples to a separation medium; separating analytes of the samples in the separation medium along a separation axis; immobilizing the analytes on a dipstick embedded in the separation medium, wherein the dipstick includes a plurality of capture regions and analytes of each sample are immobilized on a separate capture region; removing the dipstick from the separation medium; and detecting the analytes on the removed dipstick.

In some embodiments of this method, the dipstick also includes a longitudinal axis and a lateral surface; the longitudinal axis of the dipstick is aligned with the separation axis; and the capture regions of the dipstick are arrayed on the lateral surface. Here, the dipstick can be cylindrical. The capture regions can include indentations in the lateral surface, or ribs protruding from the lateral surface.

The present application also provides kits for separating and immobilizing analytes of a sample. One such kit includes a separation medium and a dipstick. The separation medium is configured for separating analytes of a sample applied thereto. The dipstick is configured to be embedded in the separation medium and subsequently removed from the separation medium. The dipstick is further configured for immobilizing analytes separated in the separation medium while embedded in the separation medium.

Another kit includes a separation medium and a dipstick embedded in the separation medium. The separation medium is configured for separating analytes of a sample applied thereto. The dipstick is configured for immobilizing analytes separated in the separation medium. The dipstick is further configured to be removed from the separation medium.

In some embodiments, these kits also include a supporting structure enclosing the separation medium or configured to enclose the separation medium. The kits can also include buffers or reagents for detecting analytes immobilized on the dipstick.

Yet another kit provided herein includes a separation medium and a supporting structure enclosing the separation medium. The separation medium is configured for separating analytes of a sample applied thereto. The supporting structure includes ribs that protrude into the separation medium and are configured for immobilizing analytes separated in the separation medium. The supporting structure is also configured to be opened and removed from the separation medium.

Further provided herein is a system for separating and detecting analytes. The system includes: a separation medium; a frame for retaining one or more dipsticks in the separation medium; a detection medium; and a motor coupled to the frame, wherein the motor is configured to remove the one or more dipsticks from the separation medium and contact the one or more removed dipsticks with the detection medium.

In some embodiments, the system also includes a stimulus for immobilizing analytes on the one or more dipsticks. Alternatively or in addition, the system can include a detector configured to detect analytes immobilized on the one or more removed dipsticks when the one or more removed dipsticks have been contacted with the detection medium. In some embodiments of the system, the motor is also configured to embed the one or more dipsticks in the separation medium.

A dipstick for immobilizing analytes of a sample is also provided herein. The dipstick includes an elongated portion, a capture agent disposed on the elongated portion, and a handle portion, wherein the elongated portion is configured to be embedded in a separation medium, and the handle portion is configured for mechanical manipulation of the dipstick.

Embodiments of the dipstick can have various features and characteristics. The elongated portion can include an electrode or magnet, a texture that increases the surface area of the dipstick, or glass, plastic, ceramic, metal, carbon fiber, graphite, or a copolymer. The elongated portion can be porous, decorated with beads, or shaped into a rod, blade, sheet, wire, needle, or thread. In some embodiments, the dipstick is electrically or thermally conductive. In other embodiments, the dipstick is electrically or thermally insulating. The capture agent of the dipstick can be a crosslinker or an affinity structure, for example. The affinity structure can include an antibody, enzyme, protein, peptide, aptamer, ligand, nucleic acid, nucleotide, nucleic acid analog, coordination complex, natural or synthetic polymer, carbohydrate, or small molecule. The capture agent can also be a membrane, which can include nitrocellulose or polyvinylidene fluoride.

In some embodiments, the dipstick includes a plurality of capture agents disposed on physically separated portions of the elongated region. In some embodiments, the handle portion includes printed markings to facilitate identification of the sample or analytes immobilized on the dipstick. The printed markings can include text, a barcode, or symbols.

Another dipstick is also provided for immobilizing analytes of a plurality of samples. This dipstick includes an elongated portion comprising a plurality of capture regions, a plurality of capture agents, and a handle portion. At least one capture agent is disposed in each capture region, the capture regions are physically separated from each other, the elongated portion is configured to be embedded in a separation medium, and the handle portion is configured for mechanical manipulation of the dipstick. In some embodiments, the capture regions are indentations in the elongated portion or ribs protruding from the elongated portion.

DETAILED DESCRIPTION OF THE INVENTION

Introduction

Figure 1:
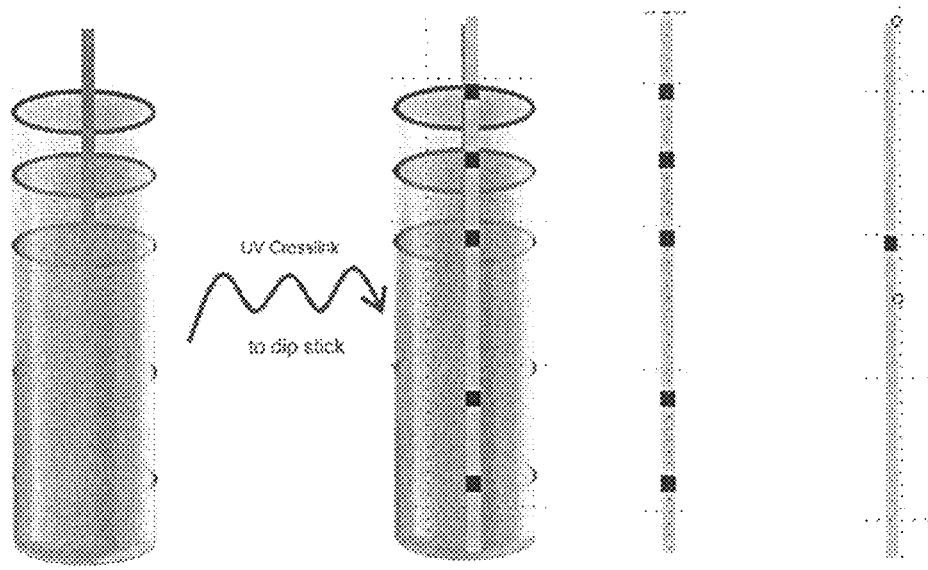
FIG. 1 shows a method of separating analytes, immobilizing analytes on a dipstick, and detecting the analytes according to some embodiments of the invention.

A convenient approach has been discovered for immobilizing analytes of a biological sample after the analytes have been separated from each other in a separation medium, such as an electrophoresis gel. The approach involves embedding a 'dipstick' structure in the separation medium and causing the analytes, or a subset thereof, to become immobilized to the dipstick in situ. The dipstick can then be removed from the separation medium and the immobilized analytes can be detected or further analyzed as desired. This approach preserves the distribution of the analytes achieved by the initial separation process, and facilitates analyte immobilization without the transfer process used in electroblotting. Furthermore, because the dipstick can be removed free and away from the separation medium, the approach provides great flexibility in analyte detection methodologies. This approach is easily multiplexed, and is simpler, less costly, and generally less problematic than electroblotting. Provided herein are dipsticks for use in embodiments of the invention. Also provided are methods, kits, and systems for separating, immobilizing, and detecting analytes using one or more dipsticks.

Definitions

'Analyte' refers to a molecule or molecular complex that can be subjected to analysis as provided herein. Analysis can include separation of a molecule from other molecules, followed by immobilization and/or detection. Analytes can be biological in origin or can be synthetic. Analytes can include peptides, proteins, nucleic acids, carbohydrates, lipids, viruses, metabolites, hormones, cofactors, vitamins, drugs, and/or small molecules. Without limitation, analytes can be polar, charged, hydrophilic, hydrophobic, monomeric, oligomeric, or polymeric and can have any molecular weight.

'Sample' refers to any biological sample that contains analytes to be separated as discussed herein. The sample can be obtained from any source, such as cells, groups of cells, tissues, or entire organisms, living or dead. The sample can be a cell lysate, tissue homogenate, or sample of blood, saliva, urine, cerebrospinal fluid, or other bodily fluid, among other possibilities. The sample can also be an in vitro preparation of molecular species, for example PCR-amplified DNA or purified proteins.

'Separation medium' refers to a material in which analytes of a sample can be separated from each other, for example by migrating through the material at different rates. The term can refer to the material used to separate analytes of a single sample, or can refer collectively to all the material used to separate analytes of multiple samples.

'Immobilize' and its grammatical equivalents refer to reducing the rate of movement of an object, such as an analyte. Immobilization of an analyte undergoing diffusive or directed motion, for example in an aqueous or gelatinous medium, can be achieved by binding the analyte to another object such as a fixed surface, by freezing the medium, or other known methods.

'Dipstick' refers to an object that can be embedded and subsequently removed from a separation medium, and to which analytes can be immobilized while the object is embedded in the separation medium. The dipstick can be embedded in the separation medium before or after separation of the analytes. The dipstick can also be configured so that some or all of the analytes can be detected while still immobilized to the dipstick.

'Capture agent' refers to a chemical moiety or a material coupled to a dipstick and by which analytes can be captured. 'Capture' can involve any kind of physical association between the analytes and capture agent, such as specific, non-specific, covalent, or non-covalent binding. Upon capture by a capture agent, analytes are immobilized on the dipstick.

'Ribs,' as used herein, refers to structures that protrude from a dipstick or the supporting structure for a separation medium. Ribs can extend along the length of a dipstick or be aligned with the separation axis in methods of separating analytes of a sample. Ribs can also be sites at which analytes are immobilized.

Methods

The current application provides methods for separating and detecting analytes of a sample using a dipstick. In some embodiments, the method includes the steps of: applying a sample to a separation medium; separating analytes of the sample in the separation medium along a separation axis; immobilizing the analytes on a dipstick embedded in the separation medium; removing the dipstick from the separation medium; and detecting the analytes immobilized on the removed dipstick. These steps are discussed below.

I. Separation

Separating analytes of the sample can be performed as desired, for example using electrophoresis, electroosmosis, or isoelectric focusing. Descriptions of these techniques can be found in Sambrook and Russell, *Molecular Cloning: A Laboratory Manual* ($3^{rd}$ ed.), New York: Cold Spring Harbor Laboratory Press, 2001 and elsewhere. Any separation medium appropriate for the chosen separation technique can be used, and this medium can have any composition, dimensions or shape. When analytes are separated using electrophoresis, for example, the separation medium can be a gel or electrolyte solution. The gel can have any desired shape or format. In some embodiments, the separation medium comprises a slab gel, tube gel, capillary, or capillary gel. In some embodiments, the separation medium comprises a gel enclosed in a cassette or adhered to a slide (such as a plastic backing) Alternatively or in addition, the gel can be open to the surrounding space on at least one side. An example of such an open gel format is an agarose gel cast in an open mold or run in an open electrophoresis rig. Other kinds of gels that can be used as the separation medium include comb gels (as described in co-pending, co-assigned U.S. patent application Ser. No. 14/558,541), mini card gels (described in e.g. WO2013/180642A1), and microfluidic chip gels (described in e.g. US2012/0329040A1). In some embodiments, the separation medium comprises a polymer matrix, hydrogel, or crosslinked polymer. Examples of crosslinked or crosslinkable polymers commonly used in gel electrophoresis are polyacrylamide and polyacrylamide-bis-acrylamide. Another example is N,N-polydimethylacrylamide, which may be preferable in capillary gel applications for reducing electroosmotic flow. Examples of polymer matrices include dextran and agarose.

As will be recognized, many variations in the composition of the separation medium are possible. The pore size of polyacrylamide gels can be varied by changing the relative concentrations of acrylamide and bisacrylamide cross-linker. Polyacrylamide gels can also be prepared with gradients of pore sizes, with separate stacking and resolving portions, or with denaturants. In some embodiments, the separation medium includes a denaturant such as sodium dodecyl sulfate (SDS) or urea to ensure that analytes such as proteins or nucleic acids remain denatured during separation. When the analytes are proteins, a reducing agent such dithiothreitol (DTT) or 2-mercaptoethanol can also be included in the separation medium to reduce disulfide bonds. Alternatively, in other embodiments, denaturants and reducing agents can be omitted to ensure that analytes retain their native structures while undergoing separation. The separation medium can have any composition compatible with immobilization and detection of analytes on the dipstick after separation.

Prior to separation, the separation medium can be enclosed in any appropriate supporting structure, and placed in contact with materials or apparatus that facilitate separation. When the separation medium is a slab gel, for example, the supporting structure can be a plastic cassette or pair of glass plates open at two ends, and the gel can be submerged at these ends in a buffer and placed in proximity to electrodes. The sample can then be applied to the separation medium as desired. Again using the example of a slab gel serving as the separation medium, the sample can be pipetted into a well formed at one end of the medium. When the separation medium includes or is enclosed by a capillary, the sample can be applied by briefly submerging one end of the medium in a solution containing the sample. Other ways of applying samples to separation media are known in the art.

In the current methods, analytes can also be separated using techniques that do not involve application of an electric field through the separation medium. One such technique is column chromatography. Here, any kind of chromatography can be used, such as size exclusion chromatography or ion exchange chromatography, as reviewed for example in Introduction to *Modern Liquid Chromatography*, 3$^{rd}$ ed., New York: Wiley, 2010. The stationary phase, enclosed in or forming part of a chromatography column, can serve as the separation medium and the dipstick can be inserted into the column. In some embodiments, the separation medium includes a chromatography resin. The sample can then be flowed through the chromatography column or resin in the mobile phase, and separation of analytes can be achieved as desired. For example, analytes of interest can be retained on the column and thereby be separated from contaminants that pass through the column. Alternatively, analytes of interest can advance through the column faster than contaminants that are more strongly retained, and be immobilized to the dipstick before they exit the column. If convenient, the composition of the mobile phase can be changed after applying the sample to the column to achieve better separation. It will be recognized that the detailed procedure needed to effectively separate analytes depends on the nature of the analytes and the makeup of the stationary and mobile phases.

Analytes can also be separated by passing the sample through a fluid channel. The channel can be a microfluidic channel or capillary, for example. Separation can be achieved by differential affinities of the analytes for the walls of the channel or for molecular entities disposed thereon. Microfluidic channels and devices can also be used to retain liquid separation media subjected to electric fields, for example for electrophoresis, as described above.

In general, analytes are separated in the separation medium along a separation axis. This axis can correspond to the direction of analyte migration in electrophoresis, the direction of mobile phase flow in column chromatography, or the direction of fluid flow in microfluidic channels. As is discussed below, the dipstick is aligned with the separation axis in some embodiments of the invention, so that the separation of analytes is preserved when the analytes are immobilized on the dipstick.

II. Immobilization

Immobilization can occur as desired, using any chemistry, catalyst, or stimulus. In some embodiments, immobilizing analytes on the dipstick includes covalently linking the analytes to the dipstick. Covalent immobilization can be accomplished using a crosslinker, which in this context is any chemical that reacts with moieties on both an analyte and the dipstick, resulting in the analyte and dipstick being linked together. Chemical crosslinkers are reviewed, for example, in Johnson and Spence (Eds.), *Molecular Probes Handbook—A Guide to Fluorescent Probes and Labeling Technologies* (11th ed.), Eugene, Oreg.: 2010, and in Hermanson, *Bioconjugate Techniques*, New York: Academic Press, 1996.

In embodiments of the present invention, homobifunctional, heterobifunctional, trifunctional, and zero-length crosslinkers can be used. Homobifunctional crosslinkers each include two identical reactive groups, such as two amines, two thiols (i.e. two sulfhydryls), two acids, or two alcohols. As appropriate, these reactive groups can react with functional groups such as amines, thiols, acids, esters, ketones, and alcohols found in biological analytes and in materials making up the dipstick. Examples of homobifunctional crosslinkers include N-hydroxysuccinimide esters and sulfo-N-hydroxysuccinimide esters, imidoesters, sulfhydryl-reactive crosslinkers (e.g. bis-maleimides), difluorobenzene derivatives, aryl azides, bis-aldehydes (e.g. glutaraldehyde), bis-epoxides, hydrazides, bis-diazonium derivates, and bis-alkylhalides (e.g. iodoacetamides). Heterobifunctional crosslinkers each include two different reactive groups and can react with disparate targets. Examples of heterobifunctional crosslinkers include N-succinimidyl 3-(2-pyridyldithio)-propionate (SPDP) and succinimidyl-4-(N-maleimidomethyl)cyclohexane-1-carboxylate (SMCC) (each reactive with amine and sulfhydryl groups), and 4-(4-N-maleimidophenyl)butyric acid hydrazide (MPBH) (reactive with carbonyl and sulfhydryl groups). Trifunctional crosslinkers, such as 4-azido-2-nitrophenylbiocytin-4-nitrophenyl ester (ABNP) and sulfo-N-hydroxysuccinimidyl-2-(6-[biotinamido]-2-(p-azido benzamido)-hexanoamido) ethyl-1,3'-dithioproprionate (sulfo-SBED), include three reactive groups. Zero-length crosslinkers facilitate or catalyze the formation of covalent bonds between two molecules but are not incorporated into the product of the crosslinking reaction. Examples of zero-length crosslinkers include carbodiimides such as 1-ethyl-3-(3-dimethylaminopropyl)carbodiimide (EDC) and dicyclohexyl carbodiimide (DCC).

In some embodiments, crosslinkers used for immobilization include photoreactive groups. These groups can react with functional groups on nearby analyte molecules upon exposure to light (FIG. 1). One such photoreactive group is benzophenone, which can attack a carbon-hydrogen bond in an analyte molecule upon UV illumination. The reaction causes displacement of the hydrogen atom and formation of a new carbon-carbon bond between the analyte and the benzophenone group. Benzophenone is one of many aryl ketones that can be used in crosslinking reactions; other aryl ketones include acetophenone, anthraquinone, anthrone, and derivates thereof. Other classes of useful photoreactive groups include quinones, aryl azides, fluorinated aryl azides, acyl azides, azido formates, sulfonyl azides, phosphoryl azides, diazo alkanes, diazoketones, diazoacetates, diazirines, and ketenes. Some reactive groups within these and related classes react spontaneously with analyte functional groups in the absence of light, and are said to be thermoreactive. These reactive groups can also be useful for crosslinking Photoreactive and thermoreactive groups can be part of bifunctional, trifunctional, or zero-length crosslinkers.

The choice of an appropriate crosslinker for immobilizing a particular analyte on a dipstick depends on the chemistry of the analyte and materials in the dipstick, as well as the environments in which these are held. Crosslinkers for use in embodiments of the invention are not limited to those listed above; any desired variations or combinations of reactive groups can be used. If analytes with disparate chemistries are to be immobilized to the same dipstick, then multiple crosslinkers can be used. Moieties on the analyte(s) and dipstick can be reacted with crosslinkers simultaneously or sequentially, with any order or timing. In some embodiments, the dipstick is pre-treated with a crosslinker, e.g. a bifunctional crosslinker, which becomes linked to the dipstick before the dipstick is exposed to analytes. Pre-treatment leaves one reactive group of the crosslinker exposed on the surface or in pores of the dipstick, available to react with analytes, and this reaction is effective to capture analytes on the dipstick.

Covalent immobilization can also occur in the absence of crosslinkers. In some embodiments, the dipstick is prepared such that reactive moieties occur directly on the surface, making a crosslinker unnecessary for immobilizing analytes. Such moieties can include the reactive groups discussed above, for example, succinimides, iodoacetamides, and maleimides, among others. Reactive moieties can be exposed on the dipstick by removing protecting groups or functionalizing the surface, for example. If desired, these moieties can be separated from the rest of the dipstick by linkers or spacers to increase accessibility for reaction, reduce steric hinderance, or reduce non-specific analyte binding. Examples of linkers include polypeptides (e.g. polyglycine or polyalanine), polymer linkers (e.g. polyethylene glycol, polyvinylpyrrolidone, polyacrylamide, polydimethylacrylamide, or dextran), dendrimers, and unbranched saturated alkyl chains. Generally, any chemistries, reaction mechanisms, or linkers, such as those provided in U.S. Pat. Nos. 6,348,596 and 7,935,489, can be used to covalently link analytes to the dipstick. For example, a functional group on the analyte can serve as a nucleophile and a moiety on the dipstick can serve as an electrophile, or vice versa. Chemistries for coupling biological analytes to various reactive moieties, materials, and surfaces are well known in the art.

Analytes can also be immobilized on the dipstick through non-covalent linkages. In some embodiments, one or more affinity structures are coupled to the dipstick and can bind non-covalently to analytes in the separation medium, thereby immobilizing these analytes. Examples of such affinity structures include antibodies, enzymes, proteins, peptides, aptamers, ligands, nucleic acids, nucleic acid analogs, coordination complexes, natural and synthetic polymers, carbohydrates, and small molecules. An affinity structure can be any kind of binding partner for an analyte of interest. If the analytes are proteins, for example, an affinity structure can be a ligand or substrate for an analyte, or an antibody that recognizes and binds specifically to an analyte. If the analytes are nucleic acids, an affinity structure can be a DNA- or RNA-binding protein, or another nucleic acid with sequence complementarity for a particular analyte. Examples of nucleic acid affinity structures include polynucleotides (single-, double-, or triple-stranded), oligonucleotides, mono-, di-, and tri-nucleotides, and nucleosides, any of which can be naturally occurring or chemically modified. Protein-based affinity structures include, in addition to antibodies, proteins such as avidin, streptavidin, and NeutrAvidin that can bind specifically to small molecules such as biotin. Small molecules such as biotin can also be used as an affinity structure, for example to bind an analyte of interest that is coupled to a small molecule-binding protein. Binding between an affinity structure and analyte can occur with any degree of affinity or specificity, although higher affinity and specificity can lead to more robust immobilization and detection.

Affinity structures can be coupled to the dipstick as desired, using any appropriate chemistry or surface treatment. In some embodiments, an affinity structure is attached to the dipstick with a linker to afford greater flexibility in analyte capture or detection. Linkers can also reduce non-specific interactions between the affinity structure or analytes with the dipstick surface. A linker can have any desired length or composition. Examples of linkers are provided above.

Immobilizing analytes on the dipstick can also include depositing the analytes on a membrane coupled to the dipstick. Here, the membrane can be analogous to that used in electroblotting, and can be treated with detectable binding partners for the analytes after the dipstick is removed from the separation medium. In some embodiments, particularly when the analytes are proteins, the membrane can include nitrocellulose or polyvinylidene fluoride. As is known in the art, these materials have affinity for proteins but do not react with them, and can bind proteins reversibly while keeping them functionally (e.g., enzymatically) active. If desired, other membrane materials having similar characteristics can be used instead or in addition. The membrane can be attached to the dipstick as desired, for example with adhesive or with fasteners, and can coat the dipstick, be wrapped around the dipstick, or be affixed to one or more individual surfaces of the dipstick. The membrane can be deposited onto the dipstick by vapor deposition, dip coating, spray coating, rolling, or printing, among other techniques.

The mechanisms available for immobilizing analytes on the dipstick are generally unrestricted and can be exploited as convenient and desired. Possible determinants of these mechanisms include the makeup of the sample being studied, the characteristics of analytes of interest (e.g., molecular weight or charge), and the composition or structure of the separation medium and dipstick. In some embodiments, analytes are immobilized on the dipstick by adsorption, electrostatic interactions, ionic interactions, or hydrophobic interactions. In some embodiments, immobilizing the analytes on the dipstick can include exposing the dipstick to light, heat, or an altered chemical environment. Light can be used to crosslink analytes to the dipstick, as discussed above, or to covalently modify analytes or their binding partners for reaction, for example by releasing UV-labile protecting groups. Heat can be used, for example, to denature analytes or contaminants from the sample or to accelerate binding reactions between analytes and moieties on the dipstick. An example of altering the chemical environment of the dipstick is submerging the dipstick, while still embedded in the separation medium, in a solution of a molecule that can simultaneously bind analytes of interest and chemical moieties on the dipstick. Another example is changing the buffer to which the dipstick is exposed and thereby exposing the dipstick to an altered pH. Thus, in some embodiments, the immobilization of analytes on the dipstick can be induced or controlled by a change in pH. Yet another example of altering the chemical environment of the dipstick is exposing the dipstick to one or more fixation reagents (also called 'fixatives') such as glutaraldehyde, formaldehyde, formalin, acetic acid, methanol, ethanol, and/or trichloroacetate that can fix (i.e., denature, crosslink, cause to aggregate, and/or cause to coagulate) proteins or other analytes, thereby immobilizing them on the dipstick. Fixation reagents can be used to complement a covalent or specific attachment mechanism and react with analytes not immobilized by this mechanism. Analytes can be immobilized on the dipstick specifically or non-specifically.

The dipstick can also include an embedded electrode, and in some embodiments analytes can be immobilized on the dipstick by energizing the electrode. This mechanism is similar to electroblotting and can be convenient when analytes are to be immobilized on the dipstick non-specifically, for example when the dipstick is coated with a membrane. The electrode can be inserted in the dipstick and connected to a power source as desired. Also if desired, a second electrode of opposite polarity can be placed away from the dipstick, in order to create an electric field effective to drive analytes from the separation medium to the dipstick. Inclusion of two electrodes in an immobilization procedure, where one electrode is inside the dipstick and one is outside, can afford greater efficiency of analyte capture on the dipstick than is possible with one electrode.

In analogy to placing an electrode inside the dipstick, the dipstick can instead or additionally include a magnet for immobilizing analytes using magnetism. Here, analyte immobilization can involve an interaction between the analytes and a magnetic field originating from the dipstick. A magnetic dipstick can be suitable for immobilizing analytes linked to magnetic labels or particles, including Dynabeads or superparamagnetic nanoparticles, by drawing these analytes toward the magnet. The magnet associated with the dipstick can be permanent, e.g. ferromagnetic, and the dipstick can be embedded in the separation medium after separating analytes so as to not interfere with the separation process. Alternatively, the dipstick can be embedded earlier in order to achieve separation and immobilization simultaneously, such that analytes are drawn through separation medium by the magnet until they reach the dipstick, where they become immobilized. The magnet associated with the dipstick can also be an electromagnet that is selectively activated at an appropriate time, for example after analyte separation has occurred. Such an electromagnet can be connected to a power source and activated as desired. The electromagnet can reside inside the separation medium during as well as after analyte separation, and be effective for immobilization while minimally disturbing separation. Other approaches to employing a magnetic dipstick in the current methods will be apparent to the skilled artisan. Like a dipstick containing an electrode, a dipstick containing a magnet can be coated with a membrane or other material to facilitate immobilization of analytes drawn to the dipstick.

Still further mechanisms of analyte immobilization include vacuum formation and capillary action. For example, a dipstick can be engineered to have a hollow core and a solid body permeable to liquid or gas. A vacuum formed in the core of the dipstick can draw the separation medium and any analytes contained therein toward and into the dipstick. Thus, the vacuum can entrap analytes in the dipstick body or immobilize analytes on the dipstick surface. The vacuum can be formed using any convenient apparatus, such as a pump. In some embodiments, any gas or liquid (for example, separation medium) drawn into the core of the dipstick can be removed, for example by a tube connecting the core to the pump through a vacuum trap. Instead or in addition, capillary action can be used for analyte immobilization on a dipstick with a porous body. When the dipstick is inserted in a liquid separation medium in which analytes have already been separated, the medium and analytes can be wicked into the dipstick body and be retained in its pores. Analytes can then remain in these pores after the dipstick is removed from the separation medium. Thus, in some embodiments analytes are immobilized using mainly mechanical rather than chemical mechanisms.

III. Detection

Once immobilized on the dipstick, analytes of the sample can be detected as desired, using any convenient technique. As discussed above, the dipstick is generally removed from the separation medium in order to carry out detection (FIG. 1). In some embodiments, analytes of interest can be detected on the dipstick if they incorporate detectable labels or are linked or conjugated to such labels. Examples of detectable labels include chromophores, fluorophores, and radioactive isotopes. Analytes can also be detected directly, in the absence of labels, if they are optically active. For example, proteins and nucleic acids absorb infrared and ultraviolet radiation and can also exhibit fluorescence. Accordingly, these analytes can be detected by directing light of an appropriate wavelength on the dipstick and measuring an interaction between the light and the analytes. For protein analytes containing tryptophan residues, fluorescence can be enhanced by contacting the analytes with any of several halo-substituted organic compounds, such as chloroform, 2,2,2-trichloroethanol, or 2,2,2-trichloroacetic acid, in the presence of UV radiation. As described in U.S. Pat. Nos. 7,569,130 and 8,007,646 and elsewhere, under such conditions a UV light-induced reaction occurs between the indole moiety of tryptophan and the halo-substituted organic compound, resulting in a fluorescent compound that emits at visible wavelengths.

Detection of immobilized analytes can make use of any labels directly or indirectly linked to the analytes, such as those described in U.S. Pat. Nos. 6,165,800, 6,395,503, 6,972,326, and 7,935,489. In some embodiments, the detected labels are fluorescent. Fluorescent dyes that can serve as labels include fluoresceins, rhodamines, coumarins, BODIPYs, and cyanines Other fluorescent dyes can be used and are reviewed, for example, in Johnson and Spence (Eds.), *Molecular Probes Handbook—A Guide to Fluorescent Probes and Labeling Technologies* (11th ed.), Eugene, Oreg.: 2010. Fluorescent dyes can be conjugated to analytes as desired, using enzymatic addition, Click chemistry, or the Staudinger ligation, among other techniques. In addition to organic dyes, quantum dots ("Q-dots") and fluorescent polymer nanoparticles (polymer dots or "P-dots") can serve as fluorescent labels. Quantum dots having any size, color, or composition can be used, and can be prepared and conjugated to analytes as desired (methods are reviewed, for example, in Medintz et al., *Nature Materials* 4: 435-446, 2005). Similarly, any polymer dots, such as those described in Wu and Chiu, *Angewandte Chemie* 52: 3086-3109, 2013 and elsewhere, can be conjugated to analytes for detection. Fluorescence can also be imparted to analytes by attaching these analytes to fluorescent proteins such as green fluorescent protein (GFP) or yellow fluorescent protein (YFP), which can serve as labels. In recombinant expression systems, a fluorescent protein can be synthesized along with a protein analyte as part of the same polypeptide, such that the fluorescent protein and analyte are covalently tethered together and one renders the other detectable.

In some embodiments, analytes are detected using chemiluminescence. These embodiments involve a chemiluminescent substrate, often a small molecule, that undergoes a chemical reaction and emits light. Some reactions of chemiluminescent substrates can be enzymatically catalyzed. For example, luminol oxidation is catalyzed by peroxidases. The light-emitting decomposition of various phosphorylated 1,2-dioxetanes is catalyzed by phosphatases, and the decomposition of galactose-substituted 1,2-dioxetanes is catalyzed by galactosidase. Tyramide derivatives, as used in tyramide signal amplification techniques, can be converted to tyrosine-reactive free radicals by peroxidases. Any of these systems, or others known in the art, can be used to detect an analyte of interest by coupling the substrate or the enzyme to the analyte. Thus, either the substrate or the enzyme can serve as a detectable label for the analyte. Upon contacting the substrate with the enzyme, light emission is colocalized with the analyte. Chemiluminescent systems from living organisms (i.e., bioluminescent systems) can also be harnessed for analyte detection. For example, luciferin can be coupled to an analyte and detected upon exposure to luciferase or aequorin. Preferably, any coupling of a chemiluminescent substrate, or an enzyme for this substrate, to an analyte for purposes of detection does not interfere with reactions of the substrate. In some embodiments, enzymes used in chemiluminescent detection are coupled to analytes of interest through biotin-avidin linkages. For example, one or more polypeptides of the enzyme can be covalently linked to avidin, and an analyte can be biotinylated. Thus, the enzyme and analyte become linked due to binding between the biotin and avidin moieties.

In other embodiments, detecting the analytes includes contacting the dipstick with a binding partner for one or more analytes of the sample, and detecting a signal indicative of binding between the binding partner and the one or more analytes. This kind of detection can be similar to that used in electroblotting (for example, Southern blotting, northern blotting, and western blotting) and can make use of detection reagents and apparatus used in electroblotting. The binding partner can include an antibody, enzyme, protein (e.g., avidin or streptavidin), peptide, aptamer, ligand, nucleic acid (e.g., nucleotide or oligonucleotide), nucleic acid analog, coordination complex, natural or synthetic polymer, carbohydrate, or small molecule (e.g., biotin). In particular, when analytes of the sample are proteins, the binding partner can be an antibody. This antibody can be directed to an epitope in one or more analytes of interest. The antibody can be detectable directly, for example by bearing a fluorescent label, or can be detectable using a secondary antibody and/or chemiluminescence. When analytes of interest are nucleic acids, the binding partner(s) can be complementary nucleic acid sequences bearing fluorescent or radioactive labels. Other probes for various types of analytes are known, and many types of signal indicative of binding can be detected. In some embodiments, the signal includes chemiluminescence, electroluminescence, fluorescence, infrared radiation, radioactivity, color, or optical absorbance. In some embodiments, the signal arises from surface plasmon resonance (SPR) and indicates an interaction between the analytes and binding partner occurring on the surface of the dipstick. Detection using SPR can employ any appropriate material on the surface of the dipstick, for example silver or gold, and can occur in the absence of an optically active moiety or label on the analytes or binding partner. In general, the analytes and binding partner can be part of a biosensor system, which can employ additional molecular components or detection apparatus.

The signal arising from the binding between an analyte and its binding partner can be amplified using any convenient technique. For example, when an analyte is detected using one or more antibodies, the signal can be amplified using tyramide radicals. The signal can also be amplified using a proximity ligation assay, in which two different oligonucleotide-linked antibodies colocalize, so that the oligonucleotides can be ligated together and amplified. Instead or in addition, one or more detectable labels, such as fluorophores, polymer dots, or quantum dots, can be conjugated to the analyte and/or binding partner to supplement signals such as those discussed above. Conjugation can employ biotin-avidin interactions, for example. If a fluorophore is coupled to each of the analyte and binding partner, and the two fluorophores have overlapping excitation and emission spectra, then binding can be detected using fluorescence quenching or fluorescence resonance energy transfer (FRET). In some embodiments, additives such as crowding agents (e.g., polyethylene glycol or dextrans) are contacted with the dipstick during detection to increase the rates of binding between an analyte and its binding partner.

If desired, two or more binding partners can be used, simultaneously or at different times, to detect analytes on the same dipstick. The binding partners can be specific for the same analyte, different forms (e.g., phosphorylated and unphosphorylated) of the same analyte, or different analytes entirely. These binding partners can give rise to the same signal, measurably different signals (for example, fluorescence of different emission wavelengths), or orthogonal types of signals (for example, fluorescence and radioactivity). Using multiple binding partners can provide more informative analyte detection than is possible with a single binding partner. For example, two binding partners can reveal the relative amounts of two different analytes immobilized on the dipstick or the relative positions of the analytes on the dipstick. Alternatively, two different antibodies directed to the same analyte can probe for the presence, integrity, or accessibility of two different epitopes.

Detecting analytes immobilized on the dipstick can require, in some embodiments, exposing the binding partner for the analytes to a reagent. The reagent can bind to or react with the binding partner in order to generate a detectable signal. For example, if the analytes are proteins and the binding partner is an antibody, the reagent can be a chemiluminescent substrate (e.g., luminol) that can be oxidized by an enzymatic domain (e.g., horseradish peroxidase) coupled to the antibody. The substrate can be added to a solution in which the dipstick is submerged, and does not become coupled to the analytes or antibody, but the chemiluminescent signal reveals the location of antibody-bound analytes. In order to amplify the light emitted by oxidation of the substrate and achieve enhanced chemiluminescence, a chemical such as p-iodophenol can also be added. When an antibody serves as binding partner to the analytes, the reagent used for purposes of detection can alternatively be a labeled secondary antibody. It will be recognized that detection can make use of multiple reagents in addition to the binding partner.

In some cases, detecting analytes on the dipstick can involve applying a blocking agent to the dipstick. The blocking agent can bind non-specifically to the dipstick, for example in locations where analytes are not immobilized, and prevent binding partners for the analytes from also binding non-specifically in these locations. The blocking agent can thus reduce background signal and allow more precise detection of analytes. Examples of blocking agents include proteins such as bovine serum albumin or milk proteins. Preferably, the blocking agent is applied to the dipstick before the dipstick is contacted with binding partners.

Any apparatus can be used to detect analytes immobilized on the dipstick, directly or with the aid of a binding partner or reagent. For example, a film or digital camera, coupled if necessary to an appropriate illumination source and/or optics (e.g., lenses, mirrors, or filters), can be used to detect color, fluorescence, chemiluminescence, and other types of optical signals arising from analytes on the dipstick. A digital camera can employ a complementary metal-oxide-semiconductor (CMOS) or charge-coupled device (CCD) detector. Images of the dipstick can be stored and processed as desired, for example to quantitate the amount of analyte present. Radioactive signals can be detected using a Geiger counter, scintillation counter, or film sensitive to isotopic decay. Other kinds of apparatus can be used in detection.

IV. Additional Steps

The method of separating and detecting analytes of a sample using a dipstick can include steps in addition to those discussed above. In some embodiments, the method also includes embedding the dipstick in the separation medium. The embedding step can occur any time before immobilizing analytes on the dipstick, and in some cases can occur before separating the analytes. In other cases, embedding the dipstick in the separation medium occurs after separating the analytes.

The optimal timing, relative to other steps in the method, for embedding the dipstick in the separation medium can depend on multiple factors. Some separation media must adopt a particular structure before separation can occur. For example, an electrophoresis gel must polymerize or congeal, and a chromatography column must be properly packed and settled. For these separation media, embedding the dipstick before separation may be convenient because it allows the structure of the medium to conform to the dipstick. For other separation media, such as liquids, that are not as structured, embedding the dipstick in the separation medium before separation may be necessary to avoid disrupting the distribution of analytes achieved by separation. However, embedding the dipstick after separation can possibly allow analytes to come into closer contact with the dipstick, and therefore be more efficiently immobilized. This would be the case if analytes avoid the dipstick while migrating through the separation medium, for example due to surface properties of the dipstick. Regardless of the timing, the dipstick can be inserted in the separation medium as desired.

In some embodiments, embedding the dipstick in the separation medium includes piercing, cutting, or slicing the separation medium. In some embodiments, the dipstick is colocalized with the separation path of the analytes at the time it is embedded in the separation medium. Alternatively, the dipstick can be placed adjacent to the separation path and/or aligned with the separation axis, and subsequently moved closer to the separation path prior to immobilization of the analytes. For example, a dipstick can be inserted between an electrophoresis gel and a supporting structure (e.g., a cassette) enclosing the gel, so that the dipstick is adjacent to one lane of the gel. The dipstick can then be moved within the supporting structure, for example in a direction perpendicular to the separation axis, so that it comes into contact with analytes that have been separated in the lane of the gel. Movement of the dipstick can include rolling, slipping, sliding, shifting, or any other kind of translocation of the dipstick with respect to the separation medium (e.g., the gel) or the supporting structure. The movement can be performed so that it does not interfere with analyte separation or the distribution of analytes achieved by separation. The movement can also prevent contamination of the dipstick with analytes in other lanes of the gel, and ensure that analytes are immobilized on the dipstick in a pattern that reflects the separation achieved in the gel (for example, the analytes remain separated by molecular weight upon being immobilized). For a given separation medium, trial and error may be needed to determine the optimal timing and mechanics for embedding and/or moving the dipstick.

The method can also involve handling control analytes, which can be used to verify that analytes become separated in the separation medium and immobilized on the dipstick as expected. Control analytes, like analytes of the sample, can be molecules of biological or synthetic origin. Control analytes can also have known or well characterized properties, including but not limited to concentration, molecular weight, charge, isoelectric point, reactivity, and monomer sequence. Preferably, the control analytes used in a particular execution of the method have properties similar to those of sample analytes applied to the separation medium.

In some embodiments, the present methods include depositing control analytes on the dipstick prior to embedding the dipstick in the separation medium. If the dipstick is then embedded in the separation medium after separation of sample analytes has occurred, then the control analytes can be used to evaluate whether sample analytes can be immobilized on the dipstick and detected. By way of example, a control analyte can be deposited, using a pipette or other implement, on a dipstick to be used for immobilizing proteins. The control analyte can be a protein having an epitope also found in a sample analyte of interest. The dipstick can then be embedded in the separation medium and immobilization and detection procedures can be carried out, for example using an antibody specific for the common epitope. If only the control analyte can be detected, then immobilization of the sample analytes may not be working or the integrity of the sample may be compromised. If neither the control analyte nor the sample analytes can be detected, then the detection of the analytes may not be working Control analytes can thus be used to troubleshoot and optimize other steps of the method. A dipstick on which control analytes have been deposited can also be embedded in the separation medium before separating analytes of the sample, to test whether analytes can migrate on the dipstick, or dissociate from the dipstick, under conditions used for separation.

Control analytes can also be used to investigate the separation process more directly. In some embodiments, the methods include the step of applying control analytes to the separation medium and separating the control analytes in the separation medium along the separation axis. Thus, control analytes can be separated in the same manner as analytes of the sample. As desired, the control analytes can be mixed with the sample analytes or can be applied to the separation medium separately. For example, if the separation medium is an electrophoresis gel with multiple lanes, then control and sample analytes can be loaded into the same lane or different lanes. Control analytes, like standards or 'ladders' used in gel electrophoresis, can be stained, radiolabeled, or otherwise marked so that they can be tracked during the separation process. The marking also allows control analytes to be detected on the dipstick using a method orthogonal to that used for detecting analytes of the sample. If desired, control analytes can be applied to the separation medium as an alternative to depositing them directly on the dipstick, or control analytes can be put in both places to better evaluate the separation, immobilization, and detection of sample analytes.

In addition, the method of separating and detecting analytes of a sample can include denaturing the analytes. 'Denaturing' as used herein has the established meaning in the art, i.e. treating analytes so that secondary, tertiary, or quaternary structure (as found in proteins or nucleic acids) is disrupted or removed. Denaturing protein or nucleic acid analytes can be useful in the current methods to ensure, for example, that these analytes separate according to molecular weight or that certain sequence motifs are accessible to binding partners. Denaturing can be performed prior to applying the sample to the separation medium, by heating the sample or applying a denaturing chemical to a buffer containing the sample. For this purpose, any such chemical such as urea or DTT can be used, and denaturing may occur as part of a larger procedure (also including, for example, filtering or resuspension) to prepare the sample for separation. Denaturing can also occur as analytes of the sample are separated, as a result of denaturants disposed within the separation medium as discussed above. Alternatively, analytes can be denatured as they are immobilized on the dipstick, for example as a result of interactions between the analytes and the surface of the dipstick, or due to exposure of the analytes to a fixation reagent as discussed above.

Some embodiments of the current methods also include a washing step, which can occur after analyte immobilization, before detection, during detection, or after detection. Washing can remove separation medium, contaminants, or unbound analytes from the dipstick, and/or stabilize immobilized analytes, alone or when bound to binding partners. Washing can involve contacting the dipstick with one or more solutions containing, for example, salts, buffering agents, protease inhibitors, chelators, ionic or non-ionic detergents (e.g., sodium dodecyl sulfate, cetrimonium bromide and other trimethylammonium bromides, polysorbate 20, and Triton X-100), alcohols, polymers, or denaturants. Washing solutions can also contain substrates or substrate analogs for any enzymes used in analyte immobilization or detection. In some embodiments, washing solutions are aqueous. Washing can also include physical agitation, rotation, rocking, or sonication of the dipstick or a solution in which it is submerged.

The current methods can be used for preparative as well as analytical purposes. To obtain a preparative quantity of one or more analytes of interest, the analytes can be eluted from the dipstick after the detection step. Elution can be performed as desired, for example by changing the chemical environment in which the dipstick is held. The dipstick can be washed in a buffer with a pH different from that used for immobilization and detection, or exposed to an enzyme that cleaves bonds anchoring analytes to the dipstick. It will be recognized that the details of an appropriate elution procedure will depend on the mechanism used to immobilize analytes on the dipstick. For greater selectivity, information obtained from detecting analytes on the dipstick can be used to concentrate elution treatments on regions of the dipstick where particular analytes of interest are localized. If desired, these regions can be cut away from the rest of the dipstick prior to elution. Alternatively or additionally, elution treatments can be applied to different regions of the dipstick at different times, so that elution proceeds in a gradual or orderly manner, for example from one end of the dipstick to the other. This approach allows analytes to be collected in fractions and maintains the separation of analytes achieved prior to immobilization, even if most or all analytes become detached from the dipstick. It will be recognized that embodiments of the dipstick can conveniently interface with analytical instrumentation, such as optical or mass spectrometers, for testing or detecting analytes after elution. Eluted analytes can also be used directly in biotechnological applications.

V. Dipsticks

Dipsticks used in embodiments of the present invention can have any desired physical characteristics. For example, a dipstick can be manufactured to any shape, have any desired dimensions, and be composed of any materials. It will be recognized that the optimal design of a dipstick, as defined above, will depend on characteristics of the separation medium in which the dipstick is embedded, the sample applied to the separation medium, and the analytes to be immobilized to the dipstick. Features of certain designs and implementations of the dipstick are now considered.

Figure 2:
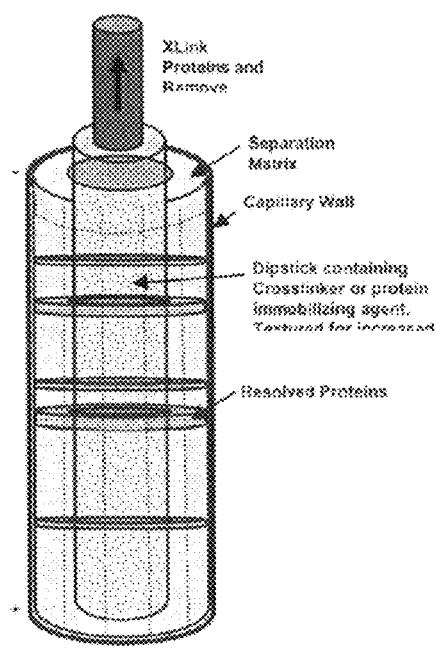
FIG. 2 shows a dipstick embedded in a separation medium according to some embodiments of the invention.

In some embodiments, the dipstick is elongated or includes an elongated portion. 'Elongated' has the standard meaning, i.e. the dipstick or a portion thereof is longer in one dimension than other dimensions. Preferably, the elongated portion is configured to be embedded in the separation medium (FIG. 2). An elongated configuration allows analytes of the sample to be spread out along the length of the dipstick as they are separated, and remain separated upon immobilization. Thus, a diversity of analytes can be immobilized, and particular analytes of interest can be well isolated. For immobilization to occur along the length of the dipstick, in some embodiments the dipstick or the elongated portion is aligned parallel to the separation axis. This alignment can also minimize the extent to which the dipstick perturbs the separation of analytes, if the dipstick is embedded in the separation medium prior to separation. For example, in a slab gel, an embedded object can interrupt the electric fields passing through the gel during electrophoresis, but aligning the object parallel to the desired direction of analyte migration can minimize such interruption.

In other embodiments, the dipstick or the elongated portion is aligned perpendicular to the separation axis. Such alignment causes most analytes to spread away from or bypass the position in the separation medium where the dipstick is embedded, so that few analytes are localized to this position after separation. However, an analyte that does become localized here can contact the dipstick, once embedded, along its entire length. Thus, if the analyte forms a band in the separation medium (for example, a gel band), and the band is also perpendicular to the separation axis, then the dipstick can contact all or nearly all of this band, rather than just a cross-section. A perpendicular alignment can be useful when only one analyte in the sample is of interest for immobilization and detection, or when capturing a large quantity of one analyte is of a higher priority than capturing smaller quantities of multiple analytes. For example, if separation occurs by isoelectric focusing and a protein having a particular pI is of interest, then a dipstick can be inserted in the separation medium at a position corresponding to the pI of the protein. A dipstick placed perpendicularly to the separation axis in the separation medium can perturb electrophoresis and other modes of analyte separation more acutely than a dipstick placed parallel, and so in some embodiments it is necessary to embed the dipstick after analyte separation.

The dipstick or an elongated portion thereof can have any of a variety of material properties. These properties can increase access of the separation medium and analytes to the dipstick, and thus lead to improved immobilization of analytes. For example, in some embodiments the dipstick is porous. This can allow the separation medium, and analytes passing through it, to penetrate the interior of the dipstick during or after the separation step. Alternatively, or in addition, the dipstick can include a texture that increases the surface area of the dipstick, again giving analytes greater access. This texture can include patterns carved on the surface of the dipstick, or small objects such as beads that coat or decorate the surface or pores of the dipstick.

To provide the desired material properties, the dipstick can be manufactured of any available materials. For example, the dipstick or the elongated portion can include glass, plastic, ceramic, metal, carbon fiber, graphite, or a copolymer. Examples of suitable metals include steel, stainless steel, iron, aluminum, titanium, copper, zinc, gold, silver, or platinum. The dipstick can be electrically and/or thermally conductive, in whole or in part, or insulating. Any manufacturing protocols can be used. It will be recognized that various materials are inert or reactive in different chemical environments, have different requirements for passivation or functionalization, and may not be suitable in all schemes for immobilizing or detecting analytes.

In some embodiments, the dipstick can be prepared as a solid with high tensile or compressive strength in the elongated dimension. Such strength can facilitate embedding the dipstick in the separation medium or removing the dipstick after analyte immobilization. If desired, the dipstick can be shaped into a rod, blade, sheet, wire, needle or thread. In some embodiments, the dipstick is needle-shaped and comprises an electrically conductive material coated with nitrocellulose.

The dipstick, or the elongated portion of the dipstick, can in some embodiments immobilize analytes through direct interactions. The dipstick can be fabricated, using appropriate materials and methods, to retain analytes through adsorption to the surface of the dipstick or absorption into the body of the dipstick. Alternatively, or in addition, the dipstick can include a capture agent. Under the definition provided above, a capture agent is any chemical moiety or material by which analytes can be captured, such that the analytes become immobilized on the dipstick. The capture agent can be used for specific or non-specific immobilization, can become linked to an analyte covalently or non-covalently, and can act reversibly or irreversibly. The capture agent can be presented on the surface of the dipstick, on beads or other objects decorating the dipstick, in pores of the dipstick, or anywhere else accessible to analytes when the dipstick is embedded in the separation medium. In some embodiments, the capture agent is a crosslinker such as benzophenone, discussed above. In other embodiments, the capture agent is an affinity structure. As discussed above, the affinity structure can be an antibody, enzyme, protein (e.g., avidin or streptavidin), peptide, aptamer, ligand, nucleic acid (e.g., nucleotide or oligonucleotide), nucleic acid analog, coordination complex, natural or synthetic polymer, carbohydrate, small molecule (e.g., biotin), or other binding partner for one or more analytes of interest. In still other embodiments, the capture agent can be a membrane such as nitrocellulose or polyvinylidene fluoride on which analytes can be deposited. Capture agents can be attached to the dipstick as desired, and multiple capture agents can be included on the same dipstick.

In addition, the dipstick or elongated portion can include an electrode or magnet, as discussed above. The electrode or magnet is preferably not exposed to the surface of the dipstick, but is disposed in the interior of the dipstick and is used to draw analytes from the surrounding separation medium to the surface. In some cases, the dipstick has a hollow core, so that the electrode or magnet can be inserted in the dipstick after the dipstick has been embedded in the separation medium, for example after analyte separation. This configuration can reduce the external dimensions of the dipstick before insertion, and prevent the electrode or magnet from perturbing any electric field imposed on the separation medium, thus allowing cleaner analyte separation. As discussed above, a dipstick bearing an electrode or magnet can be coated with a membrane, so that immobilization follows a similar mechanism to that of electroblotting.

The dipstick can also include a handle portion. In some embodiments, the handle portion is distinct from the elongated portion. The handle portion can be used for mechanical manipulation of the dipstick, such as by hand or with a robotic arm, in steps of the methods described herein. For example, the handle region can be grasped, pushed, or pulled to embed the dipstick in the separation medium, remove the dipstick from the separation medium after analyte immobilization, or expose the dipstick to binding partners for analyte detection. In some embodiments, the handle portion remains outside of the separation medium when the rest of the dipstick (or the elongated portion) is embedded in the separation medium, for ease of manipulation or to prevent contamination. The handle region can also be used for storing or providing information about experiments in which the dipstick is used. In some embodiments, the handle portion includes printed or embossed markings to facilitate identification of the sample or analytes immobilized on the dipstick. These markings can include text, a barcode, or symbols, readable by human or computer. Markings or other information can be printed on the handle portion by hand, with a label-maker, with a printer attached to a personal computer, or using other available techniques. In some embodiments, a marking can indicate a position on the dipstick, for example, the distance between the marking and the end of the dipstick. Such markings can be used to ensure that the dipstick is inserted in the separation medium at a desired position (for example, at a desired depth), and can facilitate consistent or automated analyte immobilization. Electrical contacts or positional sensors can also be installed in the dipstick, in the handle portion or the elongated portion, to aid automation.

Preferably, the elongated portion of the dipstick is designed to be smaller than the separation medium in which it is embedded, or that part of the separation medium in which analytes become distributed. For example, a dipstick designed for use with a slab gel should be thinner than the gel and no wider than one lane of the gel. Thus, the dipstick can be surrounded on nearly all sides when embedded in the separation medium, and nearly all surfaces of the dipstick can be exposed to analytes. Sizing the dipstick appropriately can lead to immobilization of more analytes and a larger signal from detection of these analytes.

In some embodiments, the separation medium is contained in a supporting structure, such as a gel cassette, capillary, or chromatography column cylinder, when the dipstick is embedded in the separation medium. Accordingly, the dipstick can be designed in view of the dimensions of the supporting structure, to comfortably fit inside. However, the dipstick need not be detached from the supporting structure and in some cases can be a part of the supporting structure. For example, if the separation medium is a slab gel, then the dipstick can be a rib on an inside wall of the gel cassette that protrudes into one of the lanes of the gel. Thus, after separating analytes in the gel, the analytes can be immobilized on this rib, and the rib can be removed from the gel upon opening the gel cassette. Other examples of integrating the dipstick with a supporting structure for the separation medium will be apparent to the skilled artisan.

Multiplexing

The methods provided herein allow multiplexing, so that analytes from multiple samples can be immobilized and detected using multiple dipsticks. As will be discussed, analytes from multiple samples can be immobilized on a single dipstick, or analytes from a single sample can be immobilized on multiple dipsticks. Many variations on the numbers of samples and dipsticks are possible. Multiplexing can allow more efficient processing of samples than is possible when examining samples one at a time, each with a single dipstick. Multiplexing can also provide more information about analytes in the samples.

Figure 3:
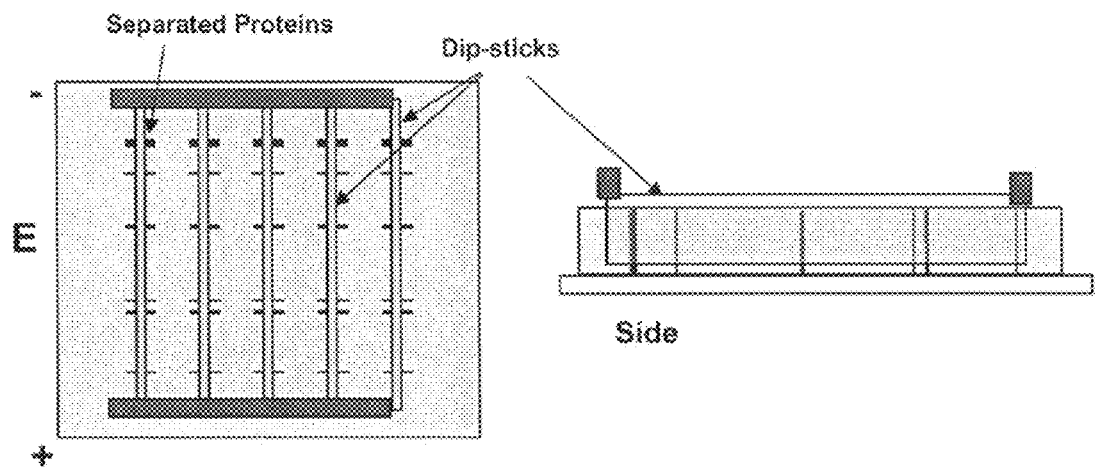
FIG. 3 shows an embodiment of multiplexed sample analysis, where one dipstick is embedded near each lane of a slab gel.
Figure 4:
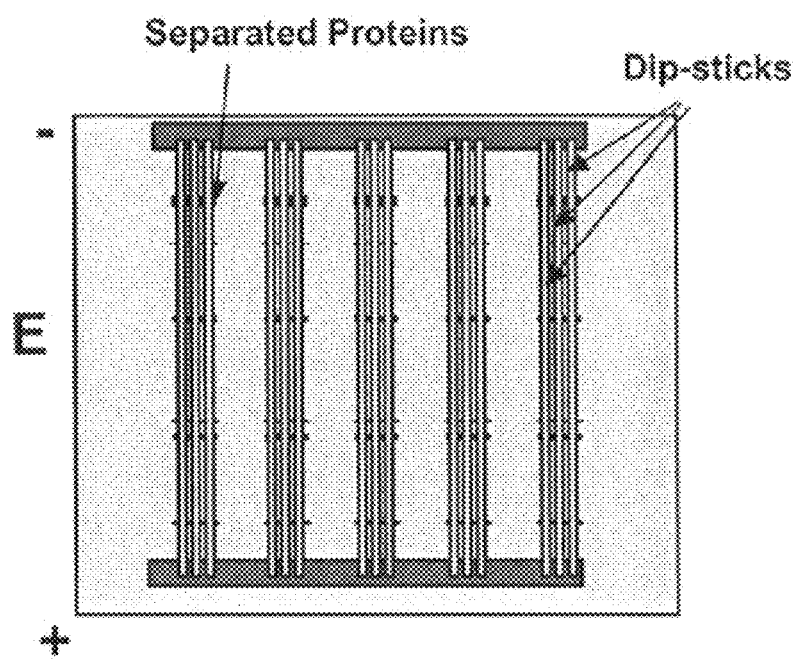
FIG. 4 shows an embodiment of multiplexed sample analysis, where multiple dipsticks are embedded near each lane of a slab gel.

In one multiplexed method, analytes of a plurality of samples are separated and detected using a plurality of dipsticks. The samples are first applied to a separation medium. The separation medium can be a slab gel or other monolithic material that can accommodate multiple samples in different locations. Alternatively, the separation medium can be a collection of capillaries or other small vessels that can each accommodate only a single sample. Analytes of the samples are then separated in the separation medium along a separation axis, as described above, and immobilized on a plurality of dipsticks embedded in the separation medium. The dipsticks can be embedded at any time prior to the immobilization of analytes, for example before or after analyte separation. At least one dipstick is associated with each sample (as in FIG. 3), and in some embodiments, multiple dipsticks are associated with a sample (as in FIG.

4). The dipsticks are then removed from the separation medium and analytes immobilized on the dipsticks are detected.

This method allows the practitioner to mix and match samples and dipsticks as desired. For example, the same sample can be applied to the separation medium in multiple places, and dipsticks configured for immobilizing different kinds of analytes can be embedded in the separation medium in these places. If desired, two or more of the plurality of dipsticks can be embedded in the same place in the separation medium, for example in the same lane of a slab gel or in the same capillary. Thus, the same sample can be interrogated for many different analytes simultaneously. Alternatively, each of the plurality of samples applied to the separation medium can have a different origin, for example taken from a different patient or cell type. The same kind of dipstick can then be embedded near each sample, in order to test each sample for a common analyte. Or dipsticks configured for immobilizing different analytes can be embedded near each sample, so that the samples can be interrogated completely independently. There is no limit to the number of dipsticks that can be embedded near and associated with each sample, provided that the dipsticks together do not prevent analyte separation, and each dipstick has sufficient exposure to the separated sample to immobilize a sufficient quantity of analytes for detection. Furthermore, the number of samples that can be multiplexed is limited only by practical considerations such as the number of gel lanes or capillaries that can be run simultaneously. In embodiments where the separation medium is a slab gel, each dipstick is preferably aligned to one lane of the gel when embedded therein, although multiple dipsticks can be aligned to the same lane.

Figure 5:
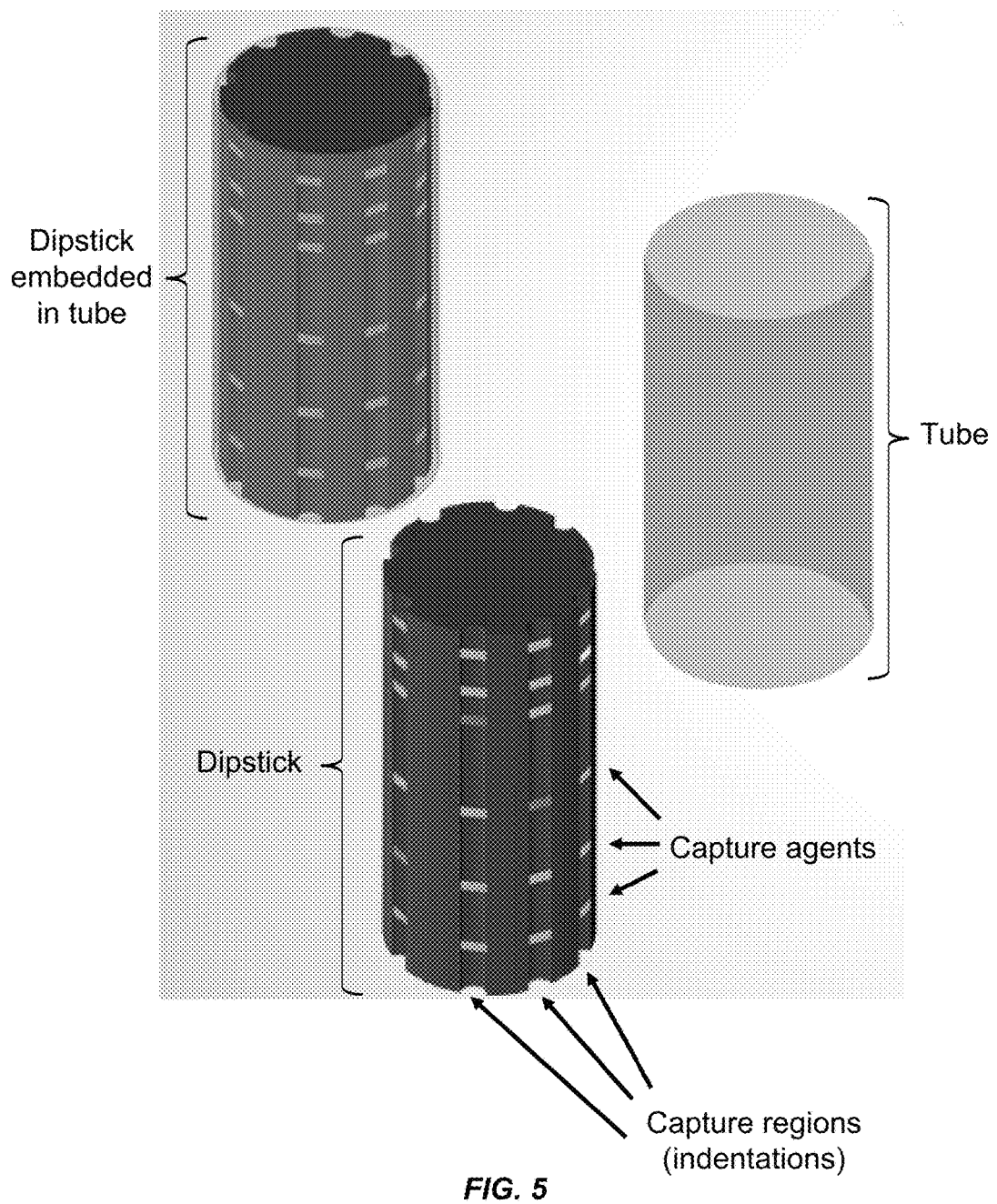
FIG. 5 shows a dipstick with multiple capture regions.

In another multiplexed method, analytes of a plurality of samples are separated and detected using a single dipstick. The dipstick includes a plurality of capture regions, which occur in distinct locations physically separated from each other. In some embodiments, the capture regions are part of the elongated portion of the dipstick. In some embodiments, the dipstick includes a longitudinal axis and a lateral surface, where the longitudinal axis is configured for alignment with the separation axis in the separation medium, and the capture regions are arrayed on the lateral surface. Such a dipstick can be generally cylindrical in shape, as shown in FIG. 5. The capture regions can be indentations in the elongated portion or lateral surface of the dipstick, or ribs protruding from the elongated portion or lateral surface. One or more capture agents, as described above, can be disposed in each capture region.

According to the method, a plurality of samples is applied to a separation medium, and analytes of the samples are separated in the separation medium along a separation axis. Analytes are then immobilized on the single dipstick embedded in the separation medium, such that analytes of each sample are immobilized on a separate capture region. The dipstick is then removed from the separation medium and analytes immobilized on the dipstick are detected.

To immobilize analytes from each sample on the same dipstick, the dipstick used in this method can be larger or shaped differently from dipsticks discussed above. In embodiments where the dipstick is cylindrical, each capture region can constitute a stripe running down the lateral surface of the cylinder. Preferably, the dipstick is embedded in the separation medium such that each capture region contacts that part of the separation medium where analytes of one sample become distributed upon separation. If the separation medium is a tube gel, for example, the dipstick can run down the middle of the gel and samples can be applied around the perimeter (FIG. 5). The capture regions can all contain the same capture agent or can contain different capture agents, as desired. In addition, more than one capture agent can be disposed in the same capture region. Thus, the dipstick can be used to interrogate the plurality of samples for one or more kinds of analytes.

Kits

Kits for use in separating and immobilizing analytes of one or more samples are also provided. The kits can be used in the methods described above or in variations thereof.

A kit according to some embodiments of the invention includes a separation medium and a dipstick. The separation medium is configured for separating analytes of a sample applied thereto. The dipstick is configured to be embedded in the separation medium and subsequently removed from the separation medium, and is configured for immobilizing analytes separated in the separation medium while embedded in the separation medium. Thus, the practitioner can use the kit to carry out the separation and immobilization steps in the methods discussed above, while inserting and removing the dipstick with respect to the separation medium at appropriate times. If desired, analytes immobilized on the dipstick can later be detected. The separation medium and dipstick can each have any of the various constitutions, characteristics, or identities discussed above, and can be used with any desired samples, reagents, or apparatus.

In other embodiments, a kit is supplied with the dipstick already embedded in the separation medium. As before, the separation medium is configured for separating analytes of a sample applied thereto. The dipstick is configured for immobilizing some or all of these analytes, and is configured to be removed from the separation medium afterward. Using this kit, the practitioner can avoid having to embed the dipstick in the separation medium before or after separating the analytes, and can thus save time. The practitioner can also avoid any problems associated with the embedding process. For example, if the dipstick is not embedded properly, the separation medium can be disrupted, such that separation of analytes does not occur or analytes cannot be immobilized on the dipstick. By embedding the dipstick in the separation medium at the factory, potential variability and error in this process is reduced.

The kits can also include a supporting structure enclosing the separation medium or configured to enclose the separation medium. The supporting structure can be a gel cassette, array of capillary tubes, chromatography column cylinder, or other similar structure as contemplated herein. The supporting structure can be designed to confine the separation medium to a volume or area appropriate for the size of the dipstick. For example, if the supporting structure is a gel cassette, the cassette can be made wider than the dipstick, so that the dipstick can fit inside the separation medium (a gel) and roughly co-localize with one lane of the gel. A kit can be received with the supporting structure already enclosing the separation medium. Alternatively, the supporting structure can be left to the practitioner to assemble around the separation medium or fill with separation medium.

A kit is also provided that includes a separation medium and supporting structure enclosing the separation medium, but no detached dipstick. Here, the supporting structure includes ribs that protrude into the separation medium and are configured for immobilizing analytes separated in the separation medium. Thus, the ribs of the supporting structure play the role of one or more dipsticks in the kits described above. The ribs can be coated or functionalized with capture agents, and can be used to immobilize analytes from one sample or multiple samples. The ribs can all target the same kind of analyte, or can target different kinds of analytes, as desired. The supporting structure is configured to be opened and removed from the separation medium after analytes have been immobilized on the ribs, so that analytes can be detected. Detection can be performed as described above.

In some embodiments, the kits include buffers or reagents for detecting analytes that are immobilized to a dipstick or supporting structure. An included buffer can be used, for example, to establish a pH or salt concentration around the dipstick at which detection can occur. The buffer can be selected in view of the particular analytes being detected or the detection means being used. Examples of reagents that can be included in the kits are antibodies, chemiluminescent substrates, and nucleic acid probes. Any of the detectable labels, binding partners, or other reagents described above for use in detection can be included in the kits.

Systems

The current application further provides systems for executing and automating the methods discussed above. According to some embodiments of the invention, a system is provided for separating and detecting analytes. The system includes a separation medium; a frame for retaining one or more dipsticks in the separation medium; a detection medium; and a motor coupled to the frame, wherein the motor is configured to remove the dipsticks from the separation medium and contact them with the detection medium.

Figure 6:
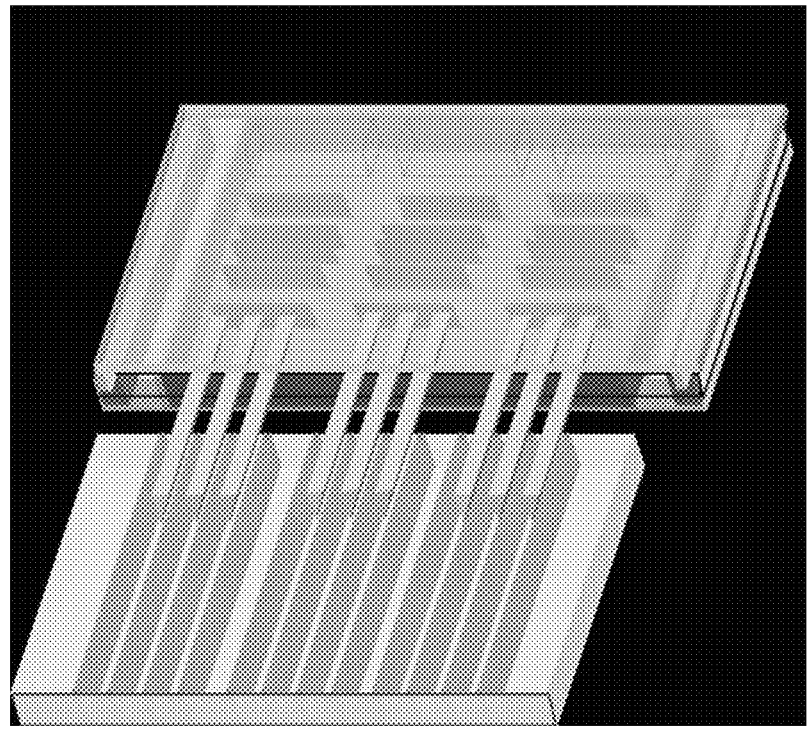
FIG. 6 shows a frame for retaining multiple dipsticks in a separation medium, according to some embodiments the invention.

The frame can be any kind of structure that holds the dipsticks in place. For example, if the separation medium is a slab gel, the frame can be analogous to a comb inserted in the gel, with the teeth of the comb replaced by dipsticks. The frame can contact the dipsticks on the handle portion, if any, or otherwise so as to not interfere with immobilization of analytes. If desired, portions of the frame can be adapted to fit and grasp individual dipsticks, as shown in FIG. 6. The motor coupled to the frame can be any kind of motor effective to move the frame relative to the separation medium upon actuation.

The detection medium is a substance, for example an aqueous solution, containing entities that facilitate detection of analytes immobilized on the dipsticks. For example, the detection medium can contain binding partners for analytes known or suspected to be in a sample applied to the separation medium, or a reagent that interacts with one of these binding partners to render it detectable. Examples of binding partners and reagents are discussed above.

In operation, the system removes the dipsticks from the separation medium, thereby automating this step, and initiates the process of detecting analytes immobilized on the dipsticks. The system supports multiplexing of sample analysis and provides convenience to the practitioner. The system can also increase the reproducibility of analyte detection. Because the mechanics of exposing a dipstick to analyte binding partners can affect the level of analyte detected, the system can reduce artifactual variability in this level from one dipstick to the next, and from one execution of the present methods to the next.

In some embodiments, the system further includes a stimulus for immobilizing analytes on the one or more dipsticks. The stimulus can be, for example, a burst of light that causes crosslinking or binding between analytes and moieties disposed on the dipsticks. The stimulus can also be a brief application of heat to accelerate immobilization, an exposure of the separation medium to a catalyst in solution, or any other treatment of the separation medium, dipsticks, and/or analytes consistent with available immobilization mechanisms. Preferably, the stimulus is applied before removing the dipsticks from the separation medium, and can be applied consistently from one dipstick to the next. Any apparatus needed to apply the stimulus, such as a light bulb or heater, can also be included in the system.

In some embodiments, the system also includes a detector configured to detect analytes immobilized on the one or more dipsticks when these have been contacted with the detection medium. The detector further automates the detection process and can further improve the reproducibility of detection. For optical detection of analytes, the detector can be a film, CCD, or CMOS camera. For detection using radioactivity, the detector can be an instrument or material sensitive to isotopic decay. Other kinds of detectors are known in the art.

The motor can also be configured to embed the one or more dipsticks in the separation medium in some embodiments of the system. Here, the movement of the motor associated with embedding can be the opposite of that associated with the removal step. Configuring the motor to embed the dipsticks in the separation medium can mitigate disruption of the separation medium from this process and improve analyte separation and immobilization.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of separating and detecting analytes of a sample, the method comprising:
   applying a sample to a separation medium, wherein the separation medium is a polyacrylamide gel;
   separating analytes of the sample in the separation medium to generate a distribution of the analytes along a separation axis;
   immobilizing the analytes on a dipstick embedded in part of the separation medium in which analytes become distributed such that the dipstick or an elongated portion thereof is aligned parallel to the separation axis, wherein distribution of analytes immobilized on the dipstick preserves the distribution of analytes as occurred in the separation medium, wherein the dipstick is embedded before the separating;
   removing the dipstick from the separation medium; and
   detecting the analytes immobilized on the removed dipstick, wherein separating analytes of the sample comprises performing electrophoresis, electroosmosis, or isoelectric focusing.

2. The method of claim 1, wherein the separation medium comprises a gel in a tube or cassette.

3. The method of claim 1, wherein the separation medium comprises a denaturant.

4. The method of claim 1, wherein immobilizing the analytes on the dipstick comprises covalently linking the analytes to the dipstick.

5. The method of claim 1, wherein immobilizing the analytes on the dipstick comprises binding the analytes to an antibody.

6. The method of claim 1, wherein immobilizing the analytes on the dipstick comprises depositing the analytes on a membrane coupled to the dipstick.

7. The method of claim 1, wherein immobilizing the analytes on the dipstick comprises exposing the dipstick to fixation reagents.

8. The method of claim 1, wherein:
the dipstick comprises an electrode, and immobilizing the analytes on the dipstick comprises energizing the electrode; or,
the dipstick comprises a magnet, and immobilizing the analytes on the dipstick comprises drawing magnetic labels linked to the analytes toward the magnet.

9. The method of claim 1, wherein detecting the analytes immobilized on the removed dipstick comprises contacting the removed dipstick with a binding partner for one or more analytes of the sample, and detecting a signal indicative of binding between the binding partner and the one or more analytes.

10. The method of claim 1, further comprising embedding the dipstick in the separation medium before separating the analytes.

11. The method of claim 1, wherein the dipstick comprises a texture or beaded coating that increases the surface area of the dipstick.

12. The method of claim 1, the analytes are proteins.

13. The method of claim 1, wherein the separating is by charge or molecular weight of the analytes.

14. The method of claim 1, wherein all of the analytes in the sample that are separated are immobilized on the dipstick.

15. The method of claim 1, wherein the detecting comprises detecting the analytes while the analytes are immobilized on the removed dipstick.

16. The method of claim 1, wherein the dipstick comprises a handle portion configured for mechanical manipulation of the dipstick.

* * * * *